(12) United States Patent
Lee

(10) Patent No.: US 7,142,738 B2
(45) Date of Patent: Nov. 28, 2006

(54) INTEGRATED ANALYTICAL BIOCHIP AND MANUFACTURING METHOD THEREOF

(75) Inventor: Gwo-Bin Lee, Tainan (TW)

(73) Assignee: National Cheng Kung University, Tainan (TW)

( * ) Notice: Subject to any disclaimer, the term of this patent is extended or adjusted under 35 U.S.C. 154(b) by 232 days.

(21) Appl. No.: 10/658,254

(22) Filed: Sep. 10, 2003

(65) Prior Publication Data

US 2004/0062468 A1 Apr. 1, 2004

(30) Foreign Application Priority Data

Oct. 1, 2002 (TW) ................................ 91122673 A

(51) Int. Cl.
 *G02B 6/12* (2006.01)
 *C12P 19/34* (2006.01)
(52) U.S. Cl. ..................... 385/14; 385/12; 435/91.2; 435/287.2
(58) Field of Classification Search .............. 385/12, 385/11, 14, 92; 435/91.2, 287.2; 422/82.11
See application file for complete search history.

(56) References Cited

U.S. PATENT DOCUMENTS 7,010,391 B1* 3/2006 Handique et al. .......... 700/266
2004/0005582 A1* 1/2004 Shipwash ..................... 435/6

* cited by examiner

*Primary Examiner*—Frank G. Font
*Assistant Examiner*—Michael P. Mooney
(74) *Attorney, Agent, or Firm*—Bacon & Thomas, PLLC

(57) ABSTRACT

The present invention provides an integrated analytical biochip and manufacturing method thereof, mainly by using a speedy and low-cost manufacturing process to integrate the Polymerase Chain Reaction ("PCR") reaction tank, Capillary Electrophoresis ("CE") channel and the fiber structure onto a single biochip, thus a DNA sample may be amplified via PCR on the biochip, and immediately driven into the CE channel for analysis in accordance with real-time online detection conducted through the fiber structure integrated on the biochip, such that a speedy and accurate process of biological sample detection and analysis can be achieved.

19 Claims, 10 Drawing Sheets

INTEGRATED ANALYTICAL BIOCHIP AND MANUFACTURING METHOD THEREOF

BACKGROUND OF THE INVENTION

1. Field of the Invention

The present invention provides an integrated analytical biochip and manufacturing method thereof, whereby utilizing the micro electromechanical system process for forming a Polymerase Chain Reaction ("PCR") micro-reaction tank, capillary electrophoresis ("CE") channels and a set of optic fiber structures on a biochip, and at the same time producing a micro temperature detector, a micro heater and an electrode for integrating with an IC controller, such that an integrated biological detection and analysis system can be formed on the same biochip.

2. Description of the Related Art

The method of utilizing PCR to clone all kinds of DNAs has already been widely applied during pre-processing procedures in biomedical detection, and the sensitivity of biomedical detection can be increased by the quantity amplified from cloning. The traditional PCR thermal cycler is operated by placing samples contained in plastic tubes into a large PCR thermal cycler for producing specific number of cycles with specific temperatures and periods of time, such that a huge quantity of DNAs can be cloned and subsequent detection can be proceeded, thus increasing the distinguishability of the biomedical detection. Yet since huge quantity of samples is required, time spent would usually be more than three hours; in contrast, the micro biomedical chip produced via MEMS process may improve the foregoing drawbacks.

It is the current trend for developing biochips to integrate the pre-detection processing mechanisms into biochips, a design that not only lowers the processing costs and decreases time spent during pre-processing procedures, but also significantly lowers the quantity of samples consumed. However, regarding reaction tanks with volume thereof less than 1 μL, it is quite a challenge to try to manufacture micro temperature control system with lower production costs, lower energy consumption, simpler manufacturing processes, higher efficiency for raising and lowering temperatures and better temperature stabilization, simply because silicon chips used in semiconductor manufacturing processes are not biologically compatible, thus time-consuming and expensive manufacturing processes have to be employed for deposition and etching. Also the temperature detector placed at the exterior of the reaction tank and the heater would cause tremendous heat inertia, such that the values obtained by the temperature detector would not be the actual temperature of the reaction sample. Furthermore, with the blocking of the reaction tank walls, the temperature gradient between the heater and the sample is caused, thus rendering the system unable to provide immediate and precise temperature control.

The conventional PCR post-processing detection method consists of steps that first retrieve the cloned DNA sample and inject the Capillary Electrophoresis ("CE") (or other detection device), so as to separate the DNA and proceed to signal measurement and detection. Yet as the quantity of PCR samples decreases to under 1 μL, the repetitious actions of injecting and retrieving would cause the decrease of the quantity of PCR samples, thus adversely affecting the detection results. Therefore it is definitely necessary to integrate the PCR and the CE on the same biochip.

Also, regarding the sample detection, the conventional optical detection method causes inconveniencies as follows:

1. The alignment in the process of the optical detection is extremely complicated and time-consuming;
2. The laser source needs to be positioned, a process that is difficult and time-consuming; and
3. The conventional optical detection device is complicated and cumbersome.

Based upon the inconveniencies mentioned above, the production costs of the conventional optical detection device are too high to proceed to commercial mass production.

Therefore, in view of various drawbacks caused by the conventional DNA sample detection and analysis methods, it is thus crucial as to how a biochip may integrate a PCR reaction tank, a CE and an optical detection system.

SUMMARY OF THE INVENTION

In view of the defects and drawbacks caused by the conventional technology, the object of the present invention is to provide an integrated analytical biochip and manufacturing method thereof, which are mainly applied in the PCR reaction, CE separation and fluorescence analysis.

The primary object of the present invention is to provide an integrated analytical biochip comprising a micro reaction tank for containing samples used in PCR reactions, a plurality of micro channels for separating the cloned samples, and a set of fiber-optical structures for detecting signals of the samples.

The micro reaction tank comprises a micro heater for heating the sample, a micro temperature detector for detecting the temperature of the sample placed in the micro reaction tank, and a set of electrodes for providing voltage and pushing the cloned sample into a micro channel via the electro-osmosis pumping.

The micro heater and the micro temperature detector are constituted by an electric resistance layer made of metal, such as, but not limited to, Pt/Cr or Pt/Ti.

The micro reaction tank further comprises an insulating layer for insulating the sample from the micro heater and the micro temperature detector so as to avoid any short circuitry, and a conductive layer for electric connection.

The insulating layer is made of material such as polyimide, Teflon, silicon dioxide ($SiO_2$), silicon nitride ($Si_3N_4$) or the like.

The metal for forming the conductive layer can be Au/Cr, Au//Ti, Ag/Cr, Ag/Ti, Al/Cr or Al/Ti, preferably Au/Cr.

The shape of the micro channel can vary such as a cross or a double cross.

The micro-reaction tank is controlled by an IC controller for providing the temperature control. The IC controller comprises a filter for filtering signals from the micro temperature detector so as to lower the value of noise and raise the ratio of signal/noise (S/N), an analog/digital converter (ADC) for converting analog signals to digital signals, and a pulse width modulator (PWM) for reading temperature signals so as to modulate the pulse width of the power source for the micro heater so as to control the temperature. The IC controller is controlled via an externally connected operating panel.

The IC controller is for processing signals from the micro temperature detector and controlling the micro heater, so as to provide variations of stable or specific temperatures.

The integrated biochip of the present invention is coupled with a power supplier for providing the IC controller power needed, and providing power for the micro heater via the IC controller. Further, the present invention is to control the electro-osmotic flow via an independent electro-osmosis controller so as to actuate the sample in the micro channel to proceed to the electrophoresis separation process. The IC controller is capable of being integrated or externally connected onto the bottom plate of a biochip.

The material that is made of the bottom plate of the biochip can be glass, quartz or polymer material such as polymethyl-methacrylate(PMMA), (polycarbonate(PC) or polydimethylsiloxane(PDMS).

The optic fiber structures comprises a pair of optic fiber channels and a pair of optic fibers, wherein the optic fibers includes a light source fiber for connecting a light source and a detecting fiber for connecting a light detector.

The light source can be laser, Hg lamp, LED or other equipment with similar functions.

The light source fiber and the detecting fiber can be multi-mode fiber or single-mode fiber, preferably the multi-mode fiber.

The other object of the present invention is to provide a manufacturing method for an integrated analytical biochip that comprises steps as follows: providing a bottom plate of the biochip; depositing metal onto the bottom plate as an electric resistance layer; depositing metal onto the bottom plate as a conductive layer; coating an insulating layer on the surfaces of the bottom plate, the electric resistance layer and the conductive layer; providing an intermediate plate and a top cover plate; etching the micro channel and the optic fiber channel on the intermediate plate and the top cover plate; drilling holes on specific positions on the intermediate plate and the top cover plate such that fluids may be led into and brought out; bonding the intermediate plate and the top cover plate so as to form the sealed micro channel and the optic fiber channels; placing the optic fibers into the optic fiber channels and fixating such; combining the bottom plate underneath the bonded intermediate plate so as to form an integrated analytical biochip.

The optic fibers comprises a light source fiber and a detecting fiber.

The material that is made of the top cover plate, the intermediate plate and the bottom plate can be glass, quartz or-polymer material such as PMMA, PC or PDMS.

The method for depositing metals can be either evaporation deposition or sputtering deposition.

The electric resistance layer is used as a micro heater, a micro temperature detector and electrodes, with the metal used being such as Pt/Cr or Pt/Ti, preferably Pt/Cr. The electrodes are for the voltage connection to the micro channel to proceed to electrophoresis and electro-osmosis flow.

The metal that the conductive layer is made of can be such as Au/Cr, Au//Ti, Ag/Cr, Ag/Ti, Al/Cr or Al/Ti, preferably Au/Cr.

The insulating layer is made of material such as polyimide, Teflon or other material with similar functions.

The etching method can be wet etching or dry etching.

BRIEF DESCRIPTION OF THE DRAWINGS

These and other features, aspects and advantages of the present invention will become better understood with regard to the following description, appended claims and accompanying drawings that are provided only for further elaboration without limiting or restricting the present invention, where:

DETAILED DESCRIPTION OF THE PREFERRED EMBODIMENT

The following is a detailed description of the best presently known modes of carrying out the inventions. This description is not to be taken in a limiting sense, but is made merely for the purpose of illustrating the general principles of the inventions.

Figure 1:
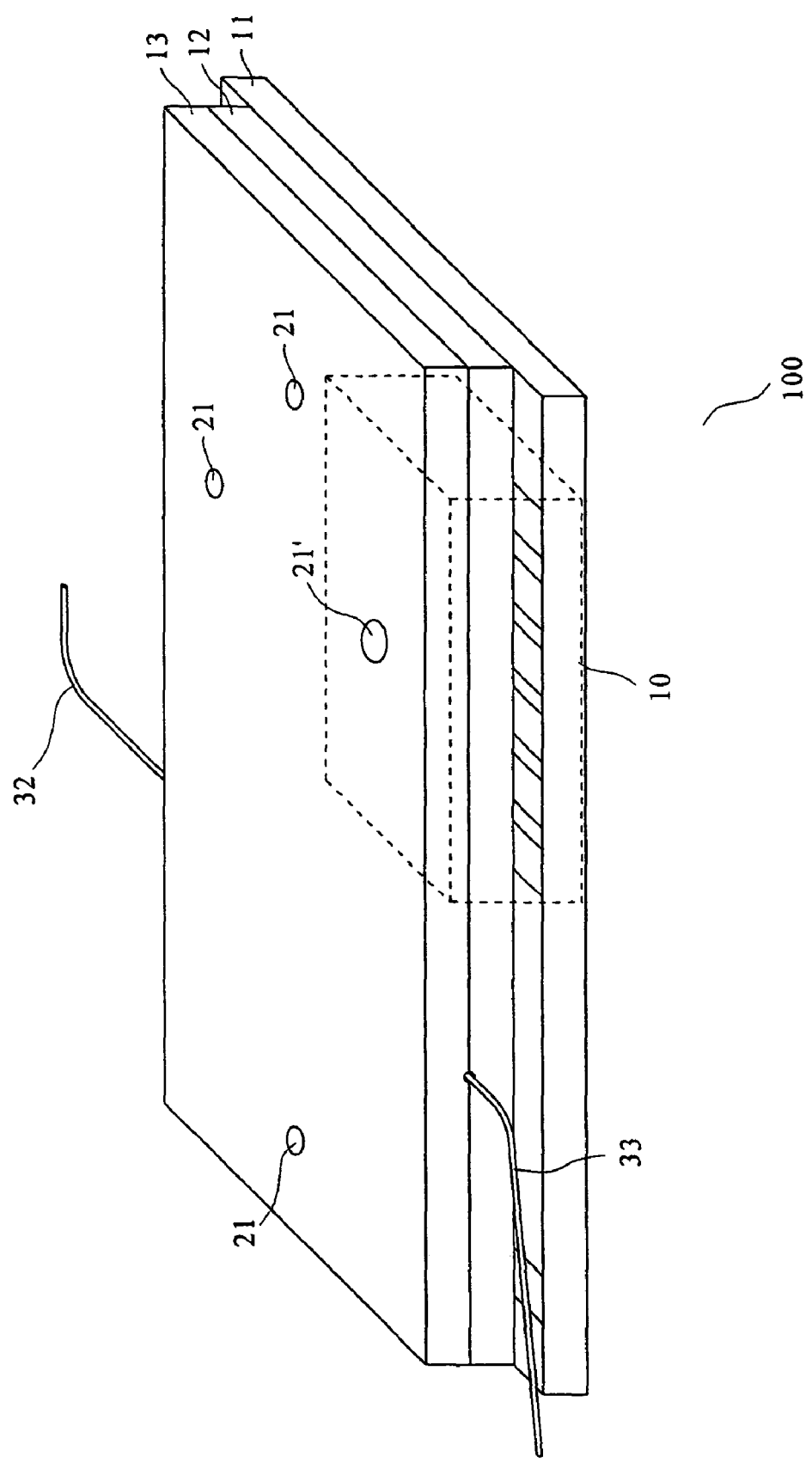
FIG. 1 shows a block diagram of an integrated analytical biochip of the present invention.
Figure 2:
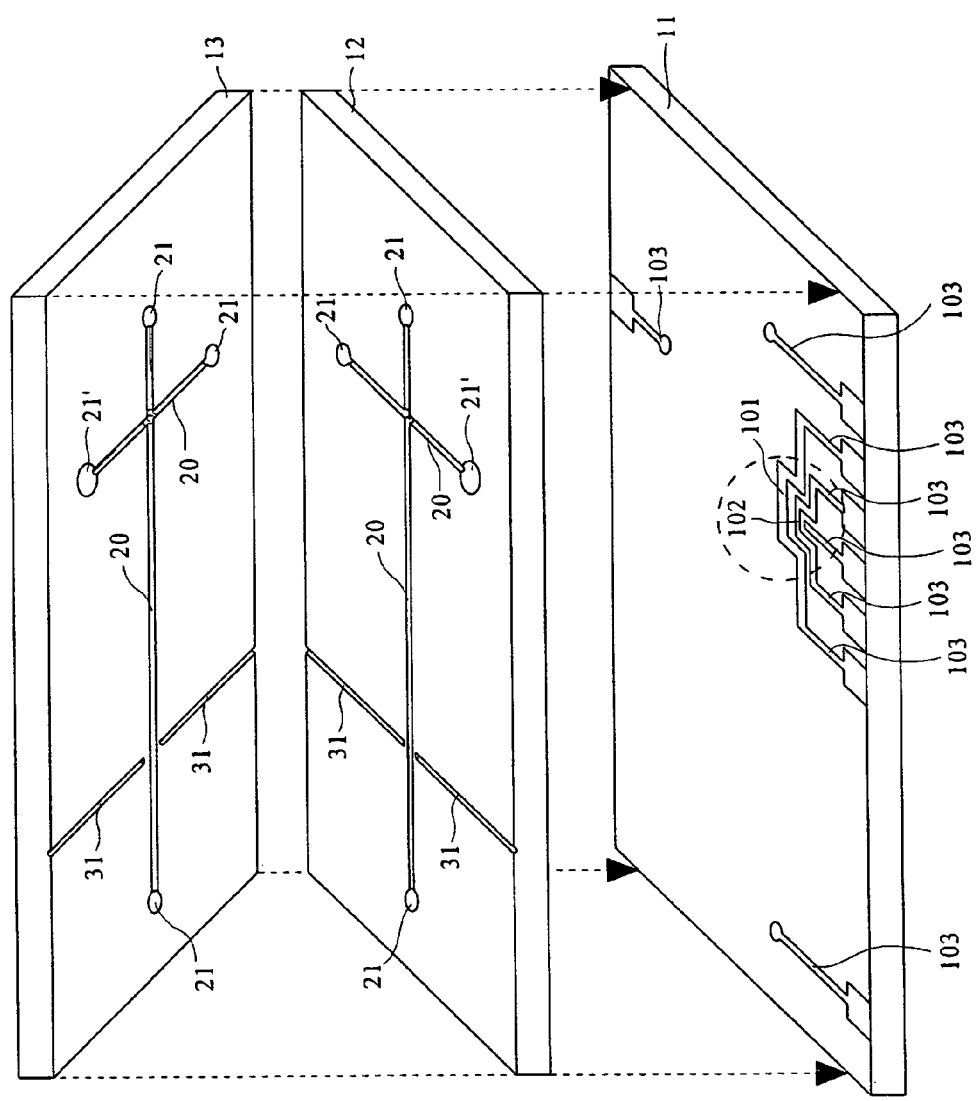
FIG. 2 shows a sectional block diagram of a top cover plate, intermediate plate and a bottom plate of an integrated analytical biochip of the present invention.

Please refer to FIG. 1 and FIG. 2. The integrated analytical biochip 100 comprises a bottom plate 11, an intermediate plate 12 and a top cover plate 13, with integrating mechanics including a micro reaction tank 10 for containing samples to proceed to PCR reactions, a plurality of micro channels 20 for separating the cloned samples, and an optic fiber structure 30 for detecting signals of samples. The micro reaction tank 10 controls the temperatures necessary for reactions via an IC controller (Not shown in drawings).

The plurality of micro channels 20, integrating the CE mechanism onto the biochip 100 for sample analysis, comprise a plurality of micro channels 20, fluid storage tank formed by aperture 21, and electrodes 103 located at the end of each micro channels 20, so as to form a CE analysis device. A power supplier (Not shown in drawings) is in accordance therewith for providing voltage so as to actuate samples. The shape of the micro channels 20 can be various, such as cross-shaped micro channels (Shown in FIG. 1 and FIG. 2) or double-cross shaped and so forth.

As shown in FIG. 2, the micro reaction tank 10 s formed by a micro heater 101 mounted on the top layer of the bottom plate 11, and a micro temperature detector 102 and electrodes also mounted on the top layer of the bottom plate 11, said temperature detector 102 and electrodes 103 being associated with apertures 21"mounted on both the intermediate plate 12 and the top cover plate 13. The micro heater 101 is for heating samples. The micro temperature detector 102 is for detecting temperatures of samples placed in the micro reaction tank 10, and the apertures 21"allow samples function as reaction tanks wherein samples are placed. The temperature of the micro reaction tank 10 is controlled via an IC control that can be externally connected or internally built on the biochip 100.

Figure 3:
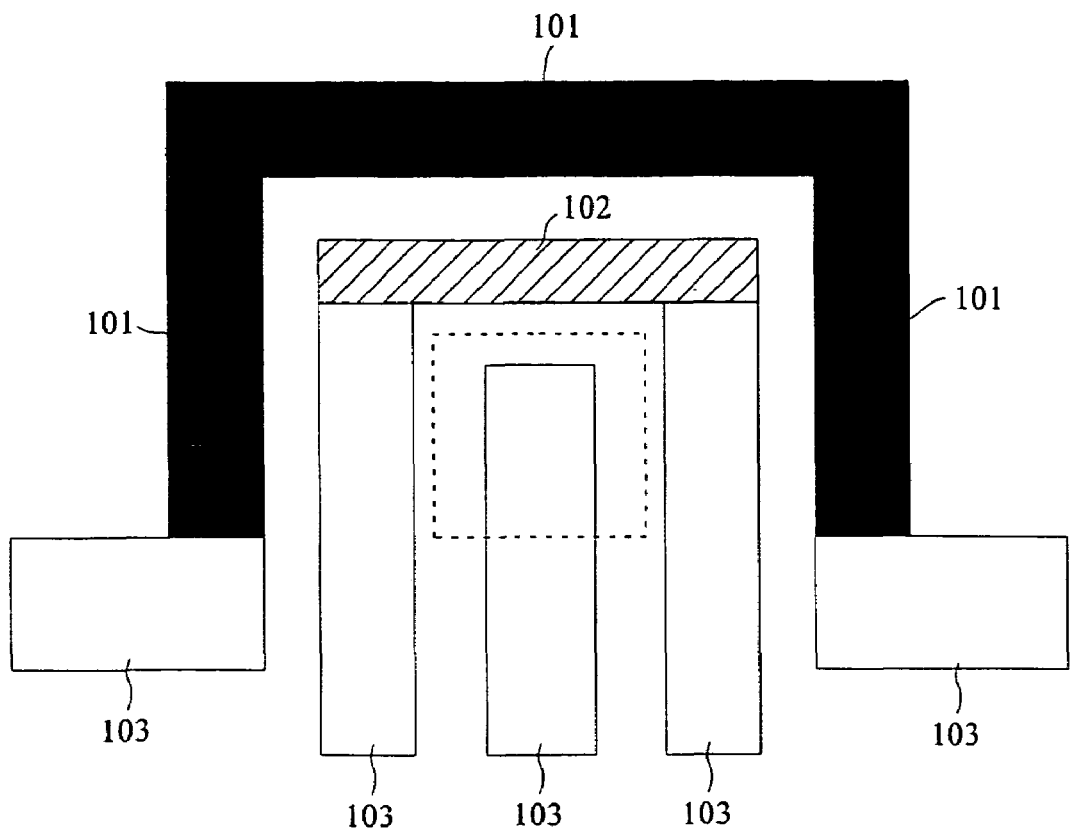
FIG. 3 shows an amplified plan view of the dotted area in FIG. 2.

FIG. 3 shows an amplified plan view of the dotted area in FIG. 2. It can be clearly understood through FIG. 3 regarding the design of the micro heater 101, the micro temperature detector 102 and the electrodes 103 on the bottom plate 11, wherein the electrodes 103 are externally connected so as to form electric connections. The dotted area in FIG. 3 is not coated with the insulating layer, such that samples can directly get into contact with electrodes 103, thus providing electrical conductivity.

Figure 4:
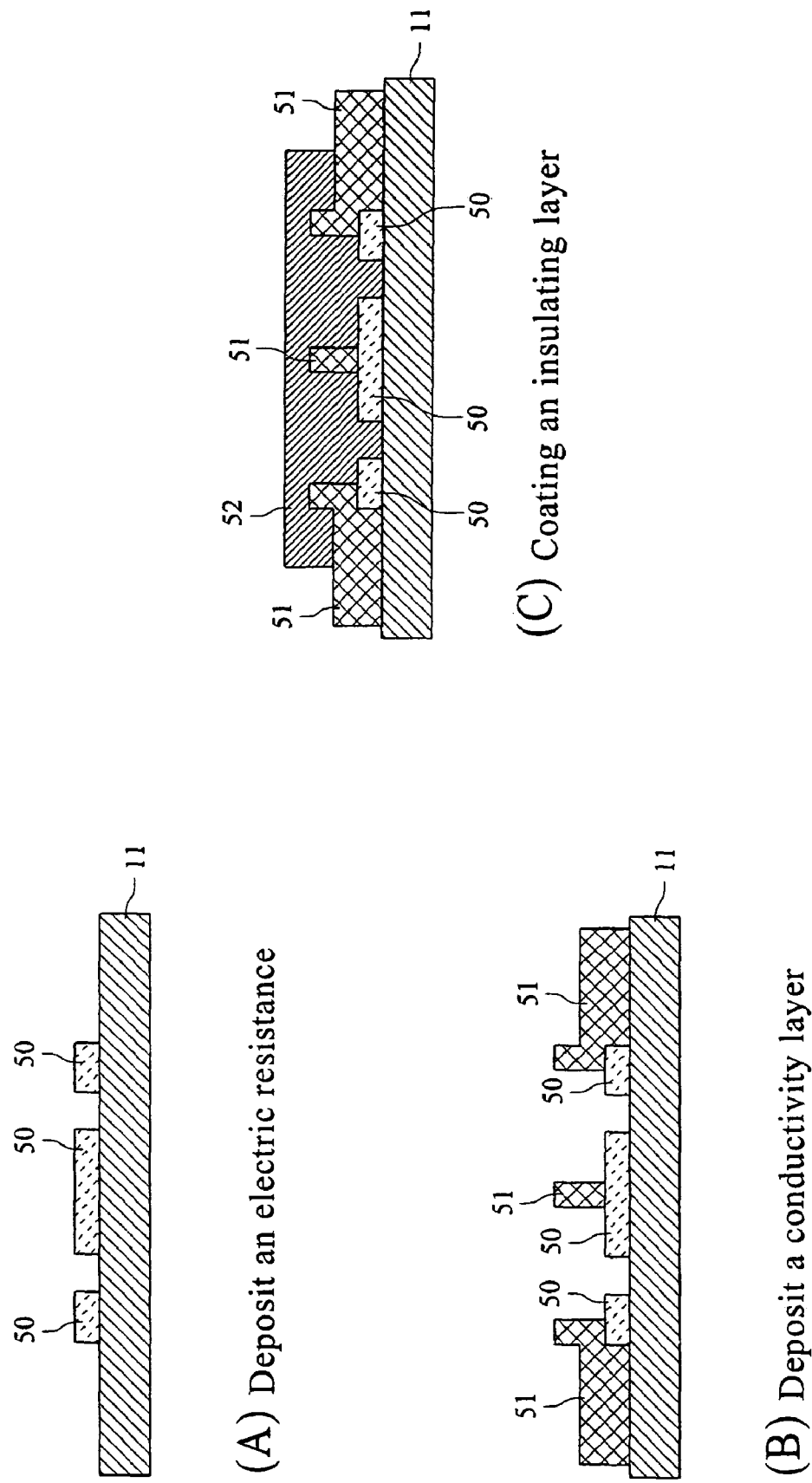
FIG. 4(A) to FIG. 4(C) shows a flowchart of the manufacturing method for a micro reaction tank on the biochip of the present invention.

The manufacturing method for the micro reaction tank 10 shown in FIG. 4(A) and FIG. 4(B) comprises steps, as follows: as shown in FIG. 4(A), providing the bottom plate 11; depositing metals (such as Pt/Cr) onto the bottom plate 11 for forming an electric resistance layer 50 that forms the micro heater 101, micro temperature detector 102 and the electrodes 103 respectively (as shown in FIG. 2). As shown in FIG. 4(B), depositing metals (such as Au/Cr) onto both the bottom plate 11 and the electric resistance layer 50 for forming a conductivity layer 51 so as to connect with the power source; as shown in FIG. 4(C), coating an insulating layer 52 on the surfaces of the bottom plate 11, the electric resistance layer 50 and the electric conductive layer 51 so as to insulate samples from both the electric resistance layer 50 and the electric conductive layer 51 for avoiding short circuitry.

The bottom plate 11 can be made of glass, quartz or polymer material such as PMMA, PC or PDMS.

The metal forming the electric resistance layer 50 can be Pt/Cr or Pt/Ti, preferably Pt/Cr.

The metal forming the conductive layer 51 can be Au/Cr, Au/Ti, Ag/Cr, Ag/Ti, Al/Cr or Al/Ti, preferably Au/Cr.

The method for depositing metals can be either evaporation deposition or sputtering deposition or other similar methods.

The insulating layer 52 is a dielectric insulating layer by using biocompatible material such as polyimide or Teflon, silicon dioxide ($SiO_2$), silicon nitride ($Si_3N_4$), preferably polyimide.

At first, the micro heater 101, micro temperature detector 102 and the electrodes 103 deposited on the bottom plate 11 are formed by the electric resistance layer that is made of metal such as, but not limited to, Pt/Cr or Pt/Ti.

Figure 5:
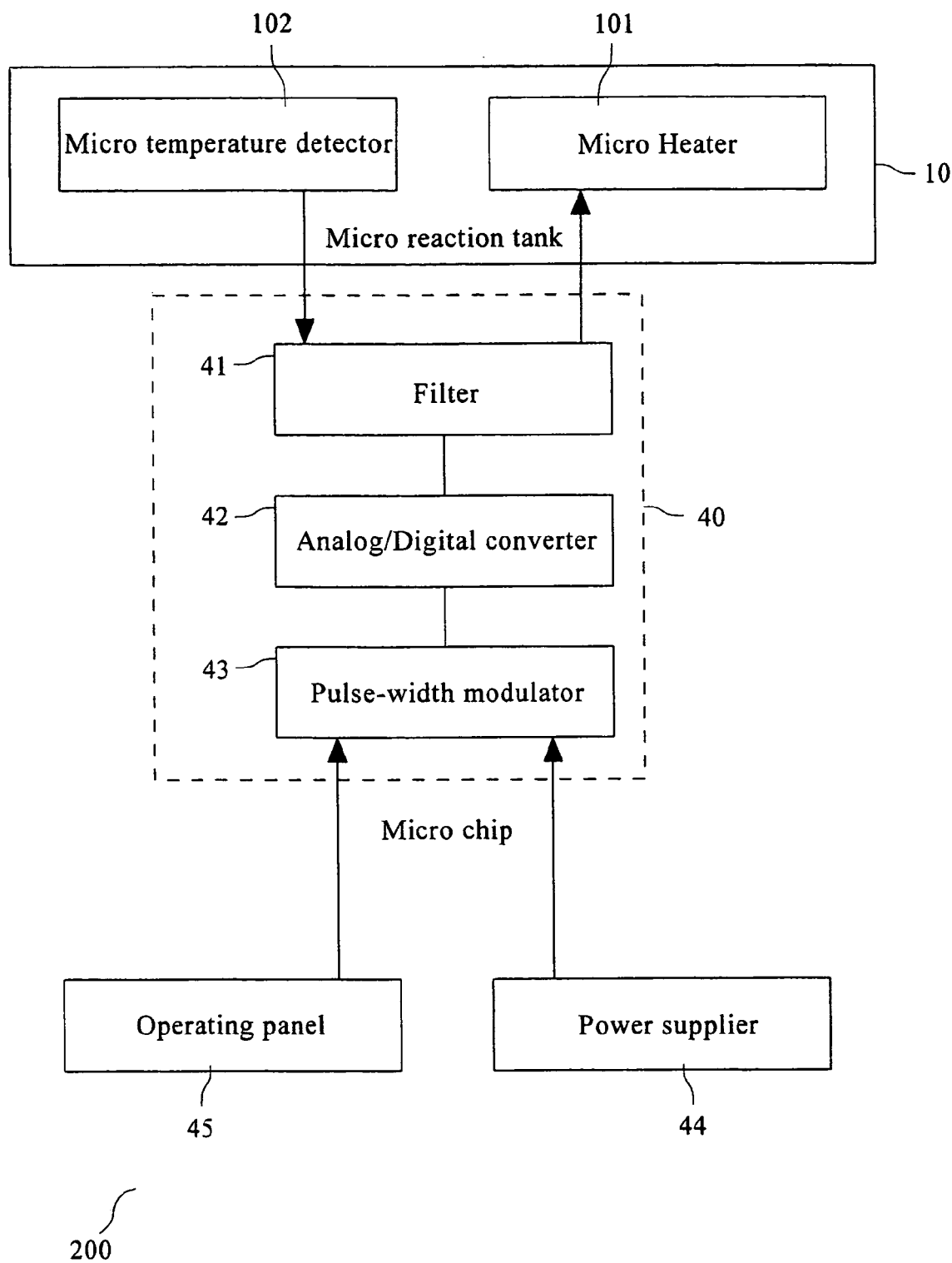
FIG. 5 shows a schematic block diagram of a temperature control system in a micro reaction tank on the biochip of the present invention.

Please refer to FIG. 5, which shows a schematic block diagram of a temperature control system 200 in a micro reaction tank 10 on the integrated analytical biochip 100 of the present invention. The main operation procedures for the temperature control system 200 are as follows: at first, samples are placed in the micro reaction tank 10, subsequently the IC controller 40 is to process signals produced via the micro reaction tank 10 and control the micro heater 101 so as to provide stable or various specific temperature variations, which are measured by the micro temperature detector 102 that transmits signals to the IC controller 40, such that, via predetermined temperature variation models installed in advance in the IC controller 40, the IC controller 40 may control the voltage pulses of the micro heater 101 basing upon temperature signals, and temperatures of samples in the micro reaction tank 10 are to be varied according to predetermined models, so that all kinds of biochemical reactions may proceed. The power source of the IC controller 40 is provided by the electric supplier 44, which also provides power to the micro heater 101 and micro temperature detector 102 via the IC controller 40.

The IC controller comprises a filter 41 for filtering signals from the micro temperature detector so as to lower the value of noise and increase the Signals/Noise ratio, an analog/digital converter (ADC) 42 so as to convert analog signals to digital signals, and a pulse-width modulator (PWM) 43 for reading temperature signals so as to modulate the pulse widths of the power source for the micro heater 101 to control temperatures. Furthermore, the IC controller 40 is controlled by an operating panel 45 externally connected for inputting data of temperatures and periods of operation.

The PCR reaction system required in cloning DNAs can be provided by using the micro reaction tank 10 in accordance with the IC controller 40 and the power supplier 44.

Figure 6:
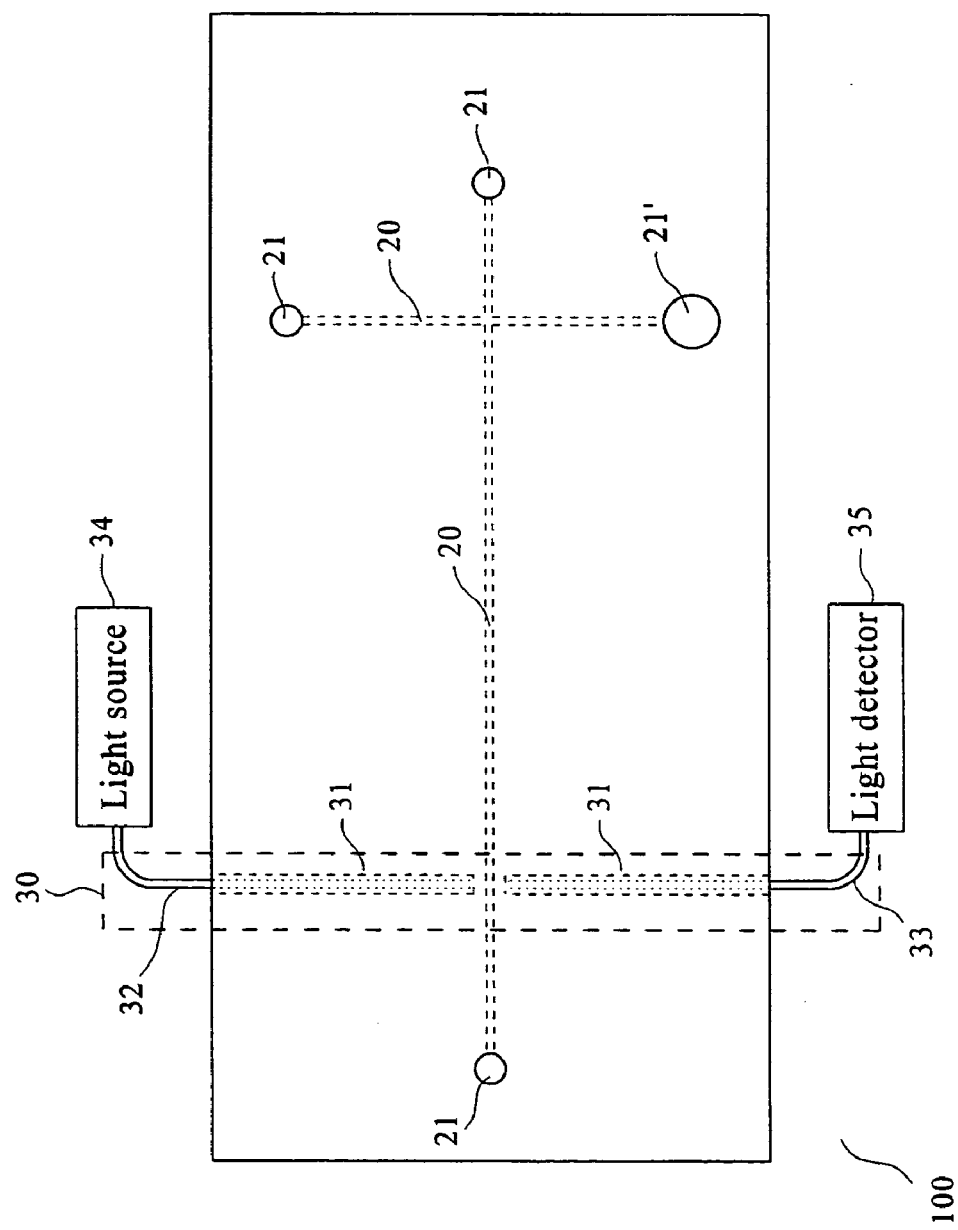
FIG. 6 shows a plan diagram of an optic fiber structure detection system on the biochip of the present invention.

As shown in FIG. 6, the fiber structure 30 on the biochip of the present invention is provided by first forming optic fiber channels 31 and then putting optic fibers 32 and 33 therein. The location of the optic fiber channel 31 on the biochip 100 and the alignment of the optic fibers 32 and 33 are both designed so as to prevent from complicated optical alignment procedures. The manufacturing process shall be elaborated subsequently. The optic fiber 32 is a light source fiber 32, whereas the optic fiber 33 is a detecting fiber 33. The light source fiber 32 is for coupling a light source 34 (such as laser), so as to enable a detection light with a specific wavelength to project into the micro channels 20, thus causing the pre-labeled DNA sample to emit induced fluorescent signals. Subsequently a light detector 35 coupled by the detecting fiber 33 goes on to measure the intensity of fluorescence of the DNA segment passing through sections of the fiber at various periods of time. The fiber structure 30 integrated on the biochip 100 can thus avoid burdensome procedures caused by conventional optical alignment and tremendously lower expenses for detecting units, and at the same time provide accurate real-time online detection.

1. The light source fiber 32 and the detecting fiber 33 are both multi-mode fiber or single-mode fiber. The other object of the present invention is to provide a manufacturing method of the integrated analytical biochip 100 comprising steps as follows: providing the bottom plate 11; depositing metal onto the bottom plate 11 as the electric resistance layer 50 for forming the micro heater 101, the micro temperature detector 102 and the electrodes 103; depositing metal onto the bottom plate 11 as the conductive layer 51; coating the insulating layer 52 on the surfaces of the bottom plate 11, the electric resistance layer 50 and the conductive layer 51; providing an intermediate plate 12 and a top cover plate 13; etching the micro channels 20 and the optic fiber channels 31 on both the intermediate plate 12 and the top cover plate 13; drilling holes at specific positions on the intermediate plate 12 and the top cover plate 13 corresponding to those of the electrodes 103 and the micro reaction tank 10 on the bottom plate 11, such that fluids may be led into and brought out and DNA samples can be placed; bonding the etched and drilled intermediate plate 12 and the top cover plate 13 so as to from the micro channels 20 and the optic fiber channels 31; placing both the light source fiber 31 and the detecting fiber 32 into the optic fiber channels 31 and fixating such by using adhesives; integrating the bottom plate 11 that are formed thereon with the micro heater 101, micro temperature detector 102 and the electrodes 103 underneath the intermediate plate 12 so as to form an integrated analytical biochip of the present invention.

The bonding of the top cover plate 13, the intermediate plate 12 and the bottom plate 11 can be achieved by using materials such as UV-sensitive glue, acrylic glue, epoxy, silicone and so forth.

Figure 7:
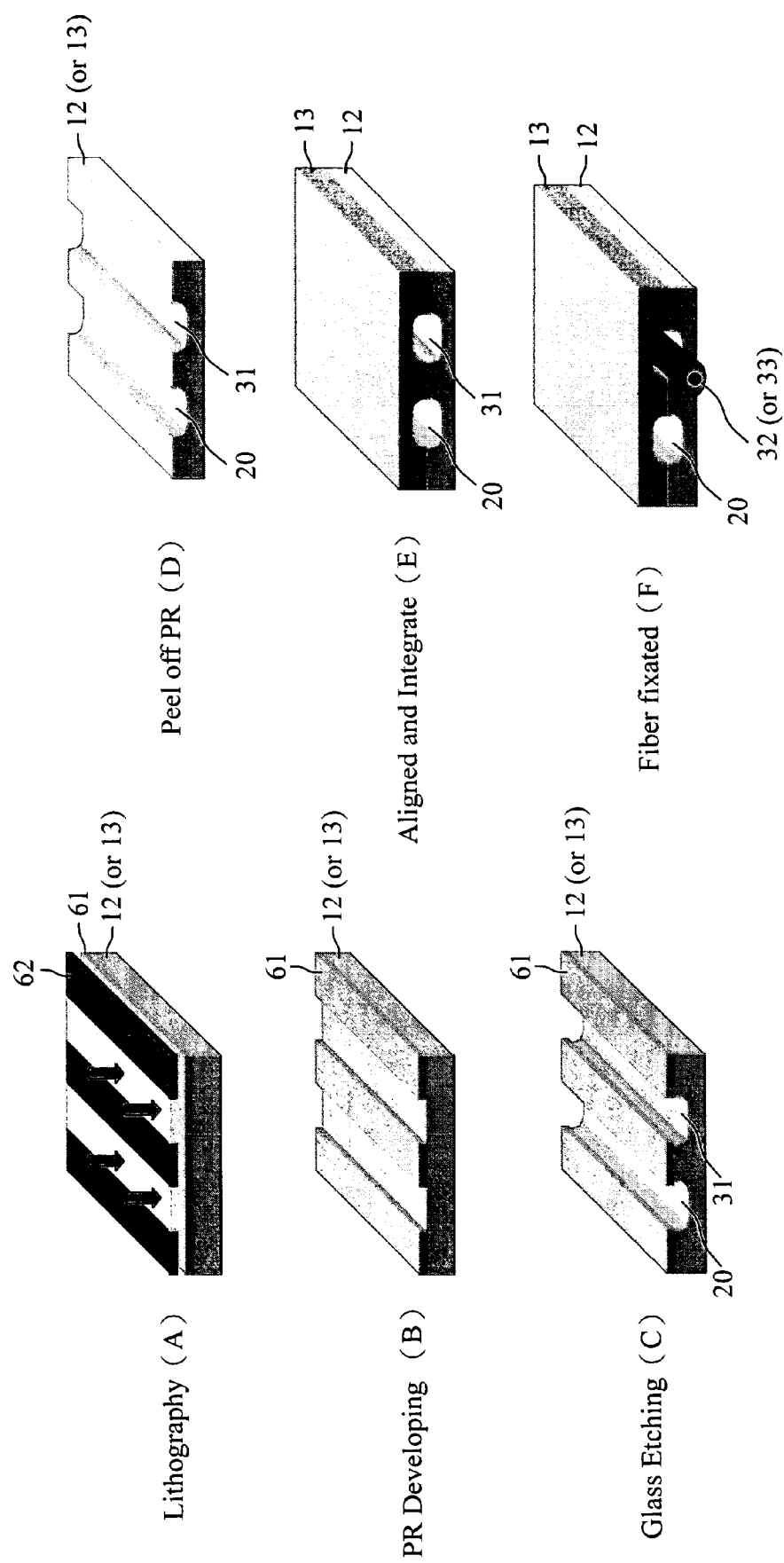
FIG. 7(A) to FIG. 7(F) shows a flowchart of the manufacturing method for a micro channel and an optic fiber structure on the biochip of the present invention.

FIG. 7 shows a flowchart of the manufacturing method for the micro channels 20 and the optic fiber channels 31 on the biochip of the present invention (The relative positions of the micro channels 20 and the optic fiber channels 31 are not to correspond to those of the design on the biochip 100), comprising steps as follows: as shown in FIG. 7(A), an intermediate plate 12 is provided whereon a photoresist layer 61 (such as AZ4620 photoresist), and a designed photomask 62 is utilized for the process of lithography. Subsequently, as shown in FIG. 7(B), the photoresist (PR) developing is processed, which is then followed by the process of glass etching for etching on the intermediate plate 12 the micro channels 20 and the optic fiber channels 31 in the predetermined specification (such as 70 μm wide and 20 μm deep). Later on, as shown in FIG. 7(D), the PR stripping is processed for cleaning any residual photoresist, which is followed by providing a top cover plate 13 and repeat the foregoing steps from FIG. 7(A) to FIG. 7(D). Subsequently, as shown in FIG. 7(E), the etched top cover plate 13 and the intermediate plate 12 are aligned and bonded so as to form the micro channels 20 and the optic fiber channels 31 on the biochip 100 of the present invention. Eventually the fibers 31 (or 32) is placed into the optic fiber channels 31 and fixated therein by stuffing adhesives such that the fiber structure 30 of the present invention is formed as shown in FIG. 7(F).

The characteristics of the present invention shall be elaborately introduced via the following embodiments.

Preferred Embodiment

The Performance Test on the Temperature Detector

Figure 8:
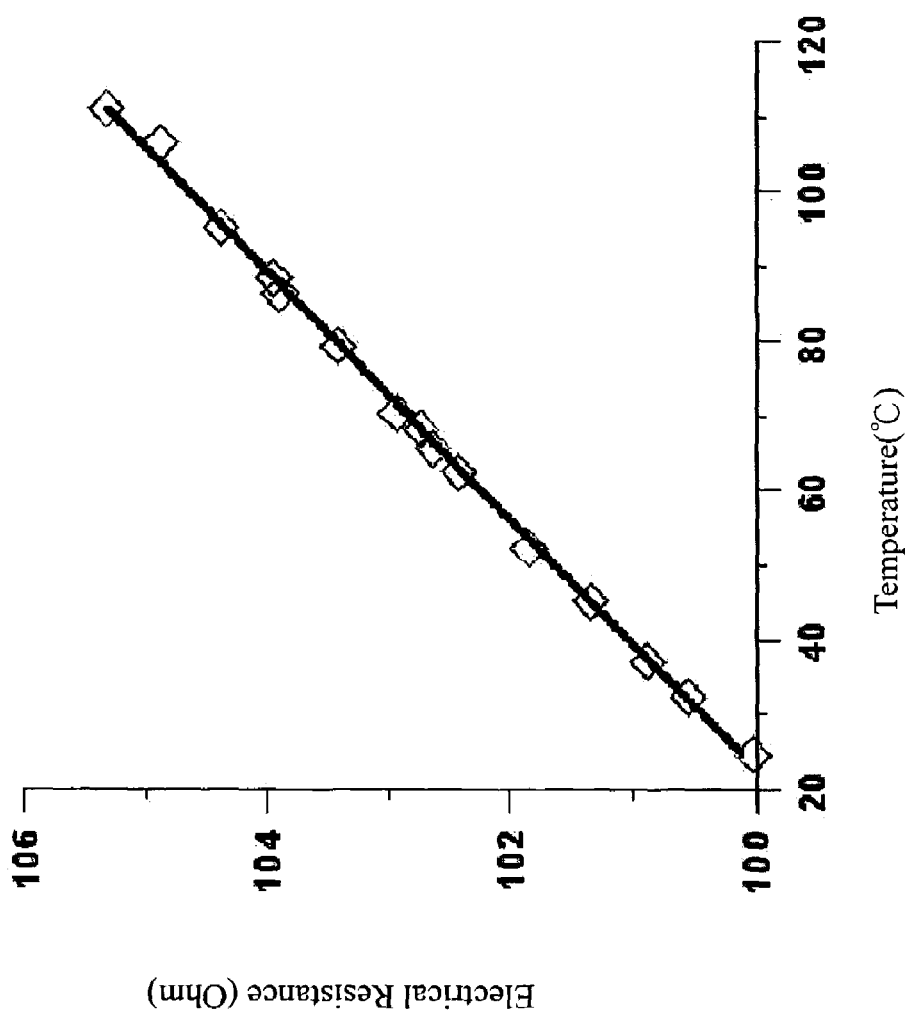
FIG. 8 shows a curve graph of the function of a temperature detector on the biochip of the present invention.

This embodiment employs the integrated analytical biochip 100 shown in FIG. 1 in accordance with the IC controller and the power supplier, with the result being shown in FIG. 8, which shows a curve graph of the function of the temperature detector on the biochip of the present invention, that the values of the electrical resistance and the temperature variations form a linear correlation with the slope (Temperature coefficient of resistance, TCR) being 0.00315/° C. Thus, accurate temperature signals can be provided within the operating range of PCR temperatures.

PCR Temperature Circulation Test

Figure 9:
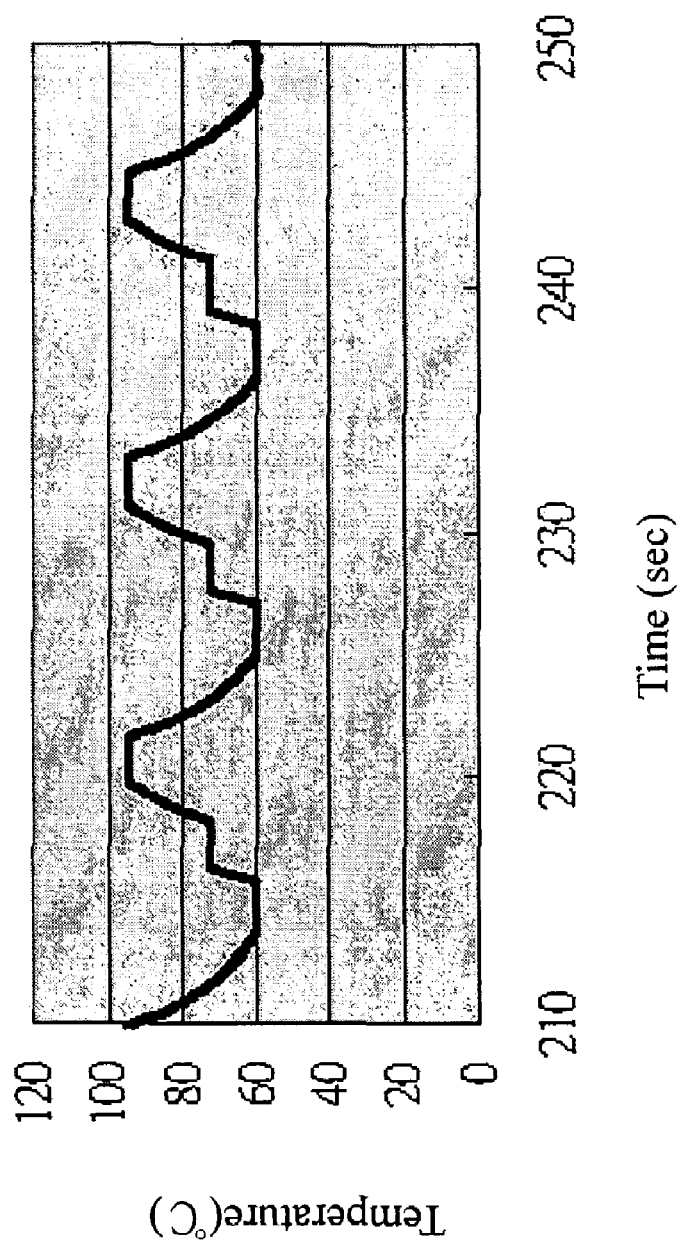
FIG. 9 shows a curve graph of the PCR thermal cycles of a micro reaction tank of the present invention.

FIG. 9 shows a curve graph of the PCR thermal cycles of the present invention, which provides the result that as the volume of a sample is 900 nL, the temperature rising rate is 20° C./sec, the temperature cooling rate is 10° C./sec, and the average power consumption is 1.24W. The micro heater in the micro reaction tank of the present invention is capable of rising and lowering the temperature within short periods of time, with the accuracy thereof being ±0.1° C., and precisely controlling the variation of temperature while the PCR reaction is proceeded in the micro reaction tank via the temperature control formula predetermined in advance in the IC controller.

The PCR Reaction and Electrophoresis Separation of DNA samples

The embodiment of the present invention utilizes a 350-bp plasmid as an example. The DNA samples (total volume of 900 nL) and designed primers are placed into the micro reaction tank of the biochip with appropriate sealing process, after which 32 times of PCR thermal cycle is conducted for 15 minutes, consequently the DNA cloning volume may reach the minimum volume required by the subsequent electrophoresis analysis.

Figure 10:
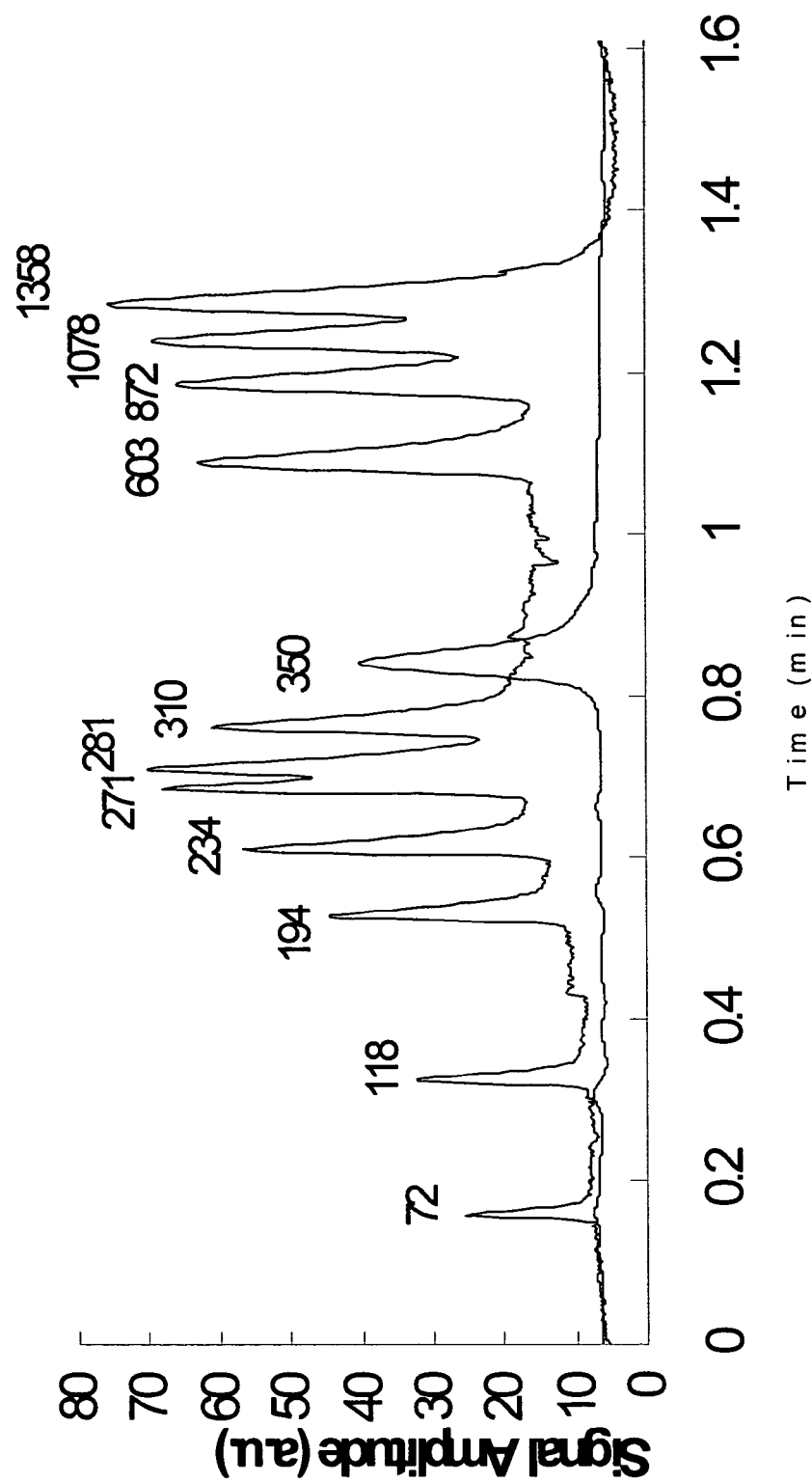
FIG. 10 shows an electrophoregram of an integrated analytical biochip of the present invention detecting DNA samples.

After the PCR reaction, the amplified DNA sample, through electro-osmosis flow produced by electric potential established by electrodes in the biochip, is driven into the micro channel for the separation process, with the injection voltage of the electrophoresis separation being 1.2 kV, the separation voltage being 2.0 kV, and the separation time being 2 minutes. Subsequently at the rear section of the micro channel, signals of the sample is detected by the fiber structure integrated on the biochip, during which the light source fiber in the fiber structure introduces the He—Ne laser detection light with a wavelength of 632.8 nm, and the detecting fiber transmits the fluorescence reaction detected to the light detector for proceeding to online real-time fluorescence signal analysis. FIG. 10 shows an electrophoregram regarding the separation of cloned DNA after PCR reaction, which provides that the effect of DNA cloning can be achieved with shorter PCR thermal cycle time by the present invention, and samples are into the micro channel in real-time fashion for electrophoresis detection analysis, eventually the online real-time fluorescence detection analysis is proceeded in accordance with the fiber structure on the biochip.

By utilizing the integrated analytical biochip of the present invention, the quantity of samples required is extremely small as being smaller than 1/20 of that used by the conventional PCR thermal cycler, such that the PCR cloning can still be proceeded with extremely small quantity of samples, and the biomedical detection analysis can immediately be conducted to the cloned DNA.

Although the present invention has been described in considerable detail with reference to certain preferred embodiments thereof, those skilled in the art can easily understand that all kinds of alterations and changes can be made within the spirit and scope of the appended claims. Therefore, the spirit and scope of the appended claims should not be limited to the description of the preferred embodiments contained herein.

What is claimed is:

1. An integrated analytical biochip comprising:
   a bottom plate, an intermediate plate, a top cover plate, and integrating mechanisms including:
   a micro reaction tank for containing samples for proceeding to PCR reaction;
   a plurality of micro channels for separating cloned samples; and
   a set of optic fiber structures for detecting signals of samples,
   wherein said micro reaction tank comprises a micro heater for heating samples, and a micro temperature detector for detecting the temperature of samples in said micro reaction tank, and wherein said micro heater and said micro temperature detector are both mounted on the same layer of said bottom plate inside said micro reaction tank.

2. The integrated analytical biochip as in claim 1, wherein variations of temperature in said micro reaction tank are controlled by an IC controller.

3. The integrated analytical biochip as in claim 1, wherein said micro heater and said micro temperature detector are formed by an electrical resistance layer.

4. The integrated analytical biochip as in claim 3, wherein said electrical resistance layer is made of Pt/Cr or Pt/Ti.

5. The integrated analytical biochip as in claim 1, wherein said micro reaction tank further comprises an insulating layer for insulating samples from said micro heater and said micro temperature detector to avoid short circuitry, and a conductive layer for electrical connection.

6. The integrated analytical biochip as in claim 5, wherein said insulating layer is made of polyimide, Teflon or other material with similar functions.

7. The integrated analytical biochip as in claim 5, wherein said conductive layer is made of metals such as Au/Cr, Au/Ti, Ag/Cr, Ag/Ti, Al/Cr or Al/Ti.

8. The integrated analytical biochip as in claim 7, wherein the metals for forming said conductive layer are au/Cr.

9. The integrated analytical biochip as in claim 2, wherein said IC controller comprises a filter for filtering signals outputted from said micro temperature detector so as to lower the value of noise and increase the signal/noise (S/N) ratio, an analog/digital converter (ADC) for converting analog signals to digital signals, and a pulse width modulator (PWM) for reading temperature signals so as to modulate the pulse width of the power source for said micro heater so as to control the temperature.

10. The integrated analytical biochip as in claim 9, wherein said IC controller is controlled via an externally connected operating panel.

11. The integrated analytical biochip as in claim 2, wherein a power supply is connected for providing the driving voltage of the electro-osmosis flow and power required by said IC controller.

12. The integrated analytical biochip as in claim 2, wherein said IC controller is integrated on or externally connected to the bottom plate of the biochip.

13. The integrated analytical biochip as in claim 12, wherein said bottom plate of the biochip is made of glass, quartz or high polymer material.

14. The integrated analytical biochip as in claim 13, wherein said high polymer material is PMMA, PC or PDMS.

15. The integrated analytical biochip as in claim 1, wherein said fiber structures comprise a pair of optic fiber channels and a pair of fibers.

16. The integrated analytical biochip as in claim 15, wherein said fibers comprise a light source fiber and a detecting fiber.

17. The integrated analytical biochip as in claim 16, wherein said light source fiber is connected with a light source, and said detecting fiber is connected to a light detector.

18. The integrated analytical biochip as in claim 17, wherein said light source is a laser, Hg lamp, LED or other equipment with similar functions.

19. The integrated analytical biochip as in claim 16, wherein said light source fiber and said detecting fiber are multi-mode fibers or single-mode fibers.

* * * * *